United States Patent [19]

Arthur

[11] Patent Number: 5,085,777

[45] Date of Patent: Feb. 4, 1992

[54] REVERSE OSMOSIS MEMBRANES OF POLYAMIDEURETHANE

[75] Inventor: Samuel D. Arthur, Wilmington, Del.

[73] Assignee: E. I. Du Pont de Nemours and Company, Wilmington, Del.

[21] Appl. No.: 586,038

[22] Filed: Aug. 31, 1990

[51] Int. Cl.5 ............... B01D 61/08; B01D 67/00; B01D 69/00; B01D 71/54
[52] U.S. Cl. .................. 210/500.38; 210/500.41; 264/DIG. 48; 264/DIG. 62; 264/4
[58] Field of Search ............... 264/41, 41.5, DIG. 62, 264/DIG. 48; 210/500.38, 500.41

[56] References Cited

U.S. PATENT DOCUMENTS 4,059,365 11/1977 Ivey et al. ............... 416/174
4,230,463 10/1980 Henis et al. ............... 55/16

FOREIGN PATENT DOCUMENTS 2626776 12/1976 Fed. Rep. of Germany .

Primary Examiner—Frank Sever

[57] ABSTRACT

The present invention is directed to an improved reverse osmosis membrane that shows surprisingly improved solute rejection and permeation properties. The membrane includes a separating layer of a polyamideurethane formed in situ by reaction of a haloformyloxy-substituted acyl haldide with a diamine-treated substrate.

27 Claims, No Drawings

REVERSE OSMOSIS MEMBRANES OF POLYAMIDEURETHANE

FIELD OF THE INVENTION

This invention relates to composite membranes for use in reverse osmosis processes such as the desalination of aqueous solutions. More particularly, the present invention relates to a multilayer membrane in which one layer is a copolymer of polyamideurethane.

BACKGROUND OF THE INVENTION

Reverse osmosis is a well known process for purification of saline water. In this process, a pressure in excess of the osmotic pressure of the saline water feed solution is applied to the feed solution to separate purified water by use of a permselective semipermeable membrane. Purified water is thereby caused to diffuse through the membrane while salt and other impurities are retained by the membrane.

Permselective membranes include composite membranes that include a separating layer on a supporting microporous substrate. The substrate is typically supported on a porous support to impart mechanical strength to the membrane. Permselective membranes suitable for use in reverse osmosis are available in various forms and configurations. Flat sheet, tubular and hollow fiber membranes are well-known in the art. These membranes can also vary in morphology. Homogenous and asymmetric membranes are operable, as well as thin film composites.

Permselective membranes are available in the form of multi-layer structures that include a membrane layer superimposed on a microporous substrate. Membrane layers which may be employed over the substrate include polyamides, polyphenylene esters, and polysulfonamides.

Polyamide discriminating layers are well-known in the art. The polyamide can be aliphatic or aromatic and may be crosslinked. Polyamide membranes may be made by the interfacial reaction of a cycloaliphatic diamine with isophthaloyl chloride, trimesoyl chloride or mixtures of these acid chlorides. Polyamide membranes also may be made by reaction of m-phenylene diamine and cyclohexane-1,3,5-tricarbonyl chloride. In addition, polyamide membrane also may be made by reaction of aromatic polyamines having at least two primary amines on an aromatic nucleus, and an aromatic polyfunctional acyl halides having an average of more than two acyl halide groups on an aromatic nucleus.

These prior art membranes, although useful as reverse osmosis membranes have, however, been prone to deficiencies such as short useful life, as well as low flux and low salt rejection. A need therefore exists for improved reverse osmosis membranes which show both high rates of salt rejection while providing improved rates of flux.

SUMMARY OF THE INVENTION

The present invention is directed to an improved reverses osmosis membrane that shows surprisingly improved solute rejection and permeation properties. The membrane includes a separating layer of a polyamideurethane formed in situ by reaction of a haloformyloxy-substituted acyl chloride with a diamine-treated substrate.

In accordance with the present invention, the improved reverse osmosis membranes are formed by treating a polymeric microporous substrate with a solution of a diamine. The treated substrate then is exposed to a haloformyloxy-substituted acyl halide in an organic solvent that is non-reactive with the polymeric substrate to provide a membrane of polyamideurethane.

The resulting membrane's surprisingly improved solute rejection and permeation properties enable the membrane to be employed in a wide variety of applications where high purity permeate is required. Examples of these applications include, but are not limited to, desalination of salt water, purified water for semiconductor manufacturing, reduction of BOD in waste water treatment, removal of dissolved salts during metal recovery, dairy processing, fruit juice concentration, de-alcoholization of wine, beer, and the like. In such applications, the liquid is placed under pressure while in contact with the improved membranes of the invention to remove impurities.

DETAILED DESCRIPTION OF THE INVENTION

Having briefly summarized the invention, the invention will now be described in detail by reference to the following specification and non-limiting examples. Unless otherwise specified, all percentages are by weight and all temperatures are in degrees centigrade.

Generally, the manufacture of the improved reverse osmosis membranes of the invention is accomplished by treating a polymeric microporous substrate with an aqueous solution of a polyfunctional amine such as m-phenylenediamine, piperazine, xylylenediamine, and the like, preferably an aromatic diamine such as p-phenylenediamine, m-phenylenediamine, and the like, most preferably m-phenylenediamine, and further treating the substrate with a solution of a haloformyloxy-substituted acyl halide such as 5-chloroformyloxyisophthaloyl chloride, 4-chloroformyloxyisophthaloyl chloride, 2-chloroformyloxyisophthaloyl chloride, bromo analogs of 5-chloroformyloxyisophthaloyl chloride such as 5-bromoformyloxyisophthaloyl dibromide, 5-bromoformyloxyisophthaloyl chloride, preferably 5-haloformyloxyisophthaloyl dihalides, most preferably, 5-chloroformyloxyisophthaloyl chloride. The reaction of the haloformyloxy-substituted acyl halide with the polyfunctional amine provides a novel composition of a polyamideurethane that shows both surprisingly improved solute rejection and improved solvent flux. The general formula of the polyamideurethane is:

$$[(CO-X-C-)_2-NH-Y-NH-]_3 \quad [X-C-]_2(NH-Y-NH-)_2 \quad [-CO-X-C-]-NH-Y-NH)_2]$$

with O, O, OH O, COOH, O groups as shown.

and low salt rejection. A need therefore exists for improved reverse osmosis membranes which show both high rates of salt rejection while providing improved rates of flux.

where
X = trivalent organic group such as tri substituted cyclo hexane, tri substituted benzene, tri substituted naphthalene, tri substituted cyclo pentane, tri substituted cyclo heptane and the like, and
Y = divalent organic group such as m-phenylene diamine, p-phenylene diamine, piperazine and the like.

Generally, the haloformyloxy-substituted isophthaloyl chlorides may be prepared by reacting an hydroxy-substituted isophthalic acid, or salts of hydroxy-substituted isophthalic acid, catalyst, phosgene, and a solvent under autogeneous pressure at elevated temperature. Preferably, the 5-chloroformyloxyisophthaloyl chloride (CFIC) that is most preferably reacted with the diamine-treated microporous substrate is prepared by heating a mixture of 25 g of 5-hydroxyisophthalic acid, 0.3 g of imidazole, 70 g of phosgene, and 100 ml of chlorobenzene solvent in a pressure vessel at 160° C. for 18 hours under autogeneous pressure. Removal of the solvent, followed by distillation of the product at 143°–151° C. and 1 mm Hg yields 12.6 g of (CFIC) (white solid, mp: 55.5°–56.5° C.).

CFIC also may be produced by using alternatives to the preferred reactants mentioned above. For example, salts of 5-hydroxyisophthalic acid such as disodium 5-hydroxyisophthalate or trisodium 5-hydroxyisophthalate may be substituted for 5-hydroxyisophthalic acid. Similarly, imidazole may be replaced with other heteroatom-containing compounds capable of complexing phosgene. Examples of such catalysts include, but are not limited to, pyridine, N,N-dimethylformamide (DMF), N,N-dimethylacetamide (DMAc), and the like. Likewise, solvents such as dioxane and methylene chloride may be employed, so long as the solvent is reasonably unreactive with the reactants and products.

CFIC is most preferred for reacting with the diamine-treated substrate to effect interfacial polymerization of polyamideurethane. However, analogs such as 5-bromoformyloxyisophthaloyl bromide, may be substituted for CFIC. Positional isomers of CFIC such as 4-chloroformyloxyisophthaloyl chloride may be substituted for CFIC. Aliphatic analogs, such as 5-chloroformyloxycyclohexane-1,3-dicarbonyl chloride may be employed as well. The haloformyloxy-substituted acyl halide also may be employed in combination with a diacyl halide to effect polymerization with a diamine to polyamideurethane; isophthaloyl chloride is an example of such a diacyl halide.

Generally, the membranes of the present invention can be manufactured by first casting a suitable substrate layer for the membrane onto a support membrane. Suitable substrate layers have been described extensively in the art. Illustrative substrate materials include organic polymeric materials such as polysulfone, polyethersulfone, chlorinated polyvinyl chloride, styrene/acrylonitrile copolymer, polybutylene terephthalate, cellulose esters and other polymers which can be prepared with a high degree of porosity and controlled pore size distribution. These materials are generally cast onto a support material of non-woven fabric or woven cloth, generally of polyester or polypropylene. Porous organic and inorganic materials also may be employed as the support material. Examples of possible support materials include, but are not limited to, nylon, cellulose, porous glass, ceramics, sintered metals, and the like. These support materials may be in the form of flat sheets, hollow tubes, hollow fibers, and the like to provide, for example, membranes in the form of fibers.

Preparation of microporous polymeric substrates is well known in the art. Preparation of microporous polysulfone that is the preferred substrate typically includes casting a solution of 15–20% polysulfone in dimethylformamide (DMF) onto a support member, followed by immediately immersing the cast material into water to produce microporous polysulfone film. The side of the polysulfone film exposed to the air during casting is called the "face" and contains very small pores, mostly under 200 angstroms in diameter. The "back" of the film in contact with the support member has very coarse pores.

After casting, the porous polysulfone substrate is treated with an aqueous polyfunctional amine, preferably, a polyfunctional aromatic amine. Aqueous m-phenylenediamine (MPD) is most advantageously employed to treat the substrate. However, other aromatic amines with sufficient water solubility to effect interfacial polymerization with haloformyloxy-substituted acyl halides also may be employed. Examples of diamines include but are not limited to p-phenylenediamine, piperazine, m-xylylenediamine, and the like. The amine-impregnated substrate is then exposed to haloformyloxy-substituted acyl halide.

In the following illustrative examples, the microporous polysulfone substrate is exposed to an aqueous solution of m-phenylenediamine (MPD) of indicated weight/volume (w/v) percent concentration at a temperature of 20° C. for 2 to 5 minutes. Advantageously, 0.5 to 3.0% by weight of aqueous MPD, and most advantageously 1 to 2% by weight of aqueous MPD, is employed. After exposure, the substrate is removed from the MPD solution, drained, and excess MPD solution removed from the substrate with a rubber roller. The MPD-treated polysulfone substrate then is exposed to a solution of a water-immiscible solvent containing a haloformyloxy-substituted acyl halide, preferably a solution of CFIC, under conditions conducive to polymerization of the polyamideurethane membrane. Suitable solvents for the haloformyloxy-substituted acyl halide are solvents which do not deleteriously affect the substrate. Examples of solvents include, but are not limited to $C_5$–$C_8$ n-alkanes, $C_4$–$C_8$ fluoroalkanes, $C_5$–$C_8$ chlorofluoroalkanes, $C_5$–$C_8$ cycloalkanes, $C_2$–$C_6$ chlorofluoroalkanes, and $C_4$–$C_8$ cyclo chlorofluoroalkanes, and Freon TF (1,1,2-trichlorotrifluoroethane). Most preferably, Freon TF is employed as the solvent for the CFIC solution.

The concentration of CFIC in the solution that is necessary to effect interfacial polymerization of polyamidurethane on the diamine-treated substrate can vary depending on the specific solvent, substrate, and the like, and can be determined experimentally. Generally, however, CFIC concentrations of 0.03–5%, preferably 0.05–0.20%, can be employed.

After formation of the polyamideurethane membrane layer, the resulting membrane is removed from the CFIC solution and drip dried for 5 to 120 seconds, preferably 60 to 120 seconds, most preferably 120 seconds. The membrane then is treated to extract impurities such as residual CFIC, residual diamine, reaction by products, and the like. This is accomplished by successively treating the membrane with water, and aqueous alkanol. Accordingly, the membrane is washed in running tap water at 20° to 60° C. preferably 40° to 60° C., most preferably 50°–55° C., for 5 to 30 minutes, preferably 10 to 20 minutes, most preferably ten minutes, and then in an aqueous lower $C_{1-3}$ alkanol, such as methanol, ethanol, isopropanol, preferably ethanol. The aqueous ethanol employed may be 5 to 25% ethanol, preferably 10 to 15% ethanol, most preferably 15% ethanol, the remainder being water. The aqueous ethanol is at 20° to 60° C., preferably 40° to 60° C., most preferably 50°–60° C. The membrane is washed in aqueous alkanol for 5 to 20 minutes, preferably 10 to 20 minutes, most preferably ten minutes. The membrane is then water-rinsed to remove ethanol.

The membrane then is stored in damp until testing for permeability and flux. Alternatively the membrane may be impregnated with a wetting agent such as glycerine to provide for dry storage and subsequent rewetting.

The membranes of the invention may be made in a variety of configurations and can be assembled in a variety of devices. Preferably, the membranes are in the form of films and fibers. For example, flat sheets of the membrane can be utilized in either plate and frame or spiral devices. Tubular and hollow fiber membranes can be assembled in generally parallel bundles in devices with tubesheets at opposing ends of the membranes. Radial, axial or down the bore flow feed can be utilized in hollow fiber devices.

The resulting membranes of polyamideurethane on a polymeric substrate such as polysulfone are evaluated for salt rejection and flux by subjecting the membranes to a feed of aqueous 0.26%–0.28% NaCl at pH 6.8 and 25°–30° C. in a cross flow permeation cell. Membranes measuring 47 mm diameter are placed into the cell and exposed to 0.75 l/minute of the aqueous NaCl solution. The membranes are exposed to feed pressure of 420 psig for at least 14 hours, after which the feed pressure is lowered to 225 psig, and the permeation properties determined. The performance of the membrane is characterized in terms of the percent of salt NaCl rejected (R), permeability (Kw), and permeate productivity. The percent salt rejected is defined as $$R = (1 - (C_p/C_f)) \cdot 100\%$$

where $C_p$ and $C_f$ are concentrations of NaCl in the permeate and feed, respectively. The concentration of the NaCl in the permeate and feed can be determined conductimetrically with a Beckman G1 conductivity cell (cell constant of 1.0), and a YSI Model 34 conductivity meter.

The permeability (Kw), defined as (flux/effective pressure), where flux is the water flow rate through the membrane and the effective pressure is equal to the feed pressure minus the opposing osmotic pressure. Flux is expressed in terms of permeate productivity, that is, in terms of (gallons of permeate/square foot membrane area/day), (GFD) at 25° C. and 225 psig. Correspondingly, permeability is expressed in terms of meters/second/teraPascal (m/s/TPa). The values of permeability, salt rejection and productivity of the membranes are given below. Conversion, expressed as volume of permeate per unit time divided by volume of feed per unit time is typically below 2%.

The membranes of this invention can be readily tailored specific applications such as removal of salt from potable water, dairy processing, and the like by varying, for example, the concentration of the haloformyloxy-substituted acyl halide employed to treat the diamine treated substrate. Accordingly, polyamideurethane layers may be formed that are suitable for achieving salt rejections from below 90 percent to more than 99 percent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth in degrees centigrade; unless otherwise indicated, all parts and percentages are by weight.

EXAMPLES 1–10

A microporous polysulfone substrate is prepared by casting a 16% solution of UDEL P3500 polyethersulfone from Union Carbide Corp. in N,N-dimethylformamide (DMF) containing 0.3% water onto a support of polyester sailcloth. The solution is cast at a knife clearance of 5.5 mil. The sailcloth bearing the cast polyethersulfone solution is immersed in a water bath within 2 seconds of casting to produce a microporous polysulfone substrate. The substrate is water-washed to remove the N,N-dimethylformamide solvent and is stored damp until use.

The microporous polysulfone substrate is immersed in an aqueous solution of metaphenylenediamine (MPD) of indicated concentration for 5 minutes. The substrate is removed, drained briefly and rolled with a rubber roller to remove surface droplets of excess MPD. The MPD-impregnated substrate then is immersed in a solution of 5-chloroformyloxyisophthaloyl chloride (CFIC) in FREON TF solvent (1,1,2-trichlorotrifluoroethane) of indicated concentrations for 20–40 seconds to form a membrane of polyamideurethane.

The membrane is removed from the CFIC solution and drip dried for 2 minutes. The membrane then is successively treated in hot (55° C.) running tap water for 10 minutes, and then in stirred 15% aqueous ethanol (50°–60° C.) for 10 minutes. The membrane is stored in water containing 0.1% sodium bicarbonate until testing for permeability and flux. The performance of the membranes formed with CFIC in solvent is reported in Table 1.

TABLE 1

| Example # | MPD Conc (%) | CFIC Conc (%) | % NaCl Rejection | Permeability Kw (m/s/TPa) | Productivity (gfd @ 225 psig) |
|---|---|---|---|---|---|
| 1 | 1.0 | 0.05 | 99.29 | 5.48 | 15.4 |
| 2 | 2.0 | 0.05 | 99.20 | 3.96 | 11.5 |
| 3 | 1.0 | 0.10 | 99.47 | 4.18 | 11.9 |
| 4 | 1.2 | 0.10 | 99.44 | 2.85 | 8.1 |
| 5 | 1.5 | 0.10 | 99.51 | 3.47 | 9.8 |
| 6 | 1.8 | 0.10 | 99.31 | 2.73 | 7.8 |
| 7 | 2.0 | 0.10 | 98.95 | 3.98 | 11.3 |
| 8 | 1.0 | 0.15 | 99.76 | 2.92 | 8.2 |
| 9 | 1.5 | 0.15 | 99.74 | 3.31 | 9.3 |
| 10 | 2.0 | 0.15 | 99.47 | 3.19 | 9.1 |

The effect of feed pH on NaCl rejection is determined for the membranes of Examples 4 and 5 by adjusting the 0.27% NaCl feed pH with HCl and NaOH. The results are given in Table 2.

TABLE 2

| Example # | Membrane of Example # | pH 6.8 % NaCl Rej | pH 3.5 % NaCl Rej | pH 4.0 % NaCl Rej | pH 4.9 % NaCl Rej | pH 6.8 % NaCl Rej |
|---|---|---|---|---|---|---|
| 11 | 4 | 99.34 | 89.40 | 95.18 | 99.17 | |
| 12 | 5 | 99.64 | 91.89 | 95.24 | 99.34 | 99.70 |

Examples 13–16 set forth in Table 3 illustrate the performance of membranes produced by treating an MPD-treated support with a CFIC solution of indicated concentration that includes the indicated concentration of a 70:30 blend of iso- and terephthaloyl (I/T) chloride under the conditions of Examples 1-10.

TABLE 3

| Example # | MPD Conc % | CFIC Conc % | I/T Conc % | % NaCl Rejection | Permeability Kw (m/s/TPa) | Productivity (gfd @ 225 psig) |
|---|---|---|---|---|---|---|
| 13 | 1.0 | 0.05 | 0.10 | 98.53 | 3.5 | 10.0 |
| 14 | 1.0 | 0.15 | 0.10 | 99.64 | 3.0 | 8.5 |
| 15 | 2.0 | 0.05 | 0.10 | 98.70 | 3.0 | 8.5 |
| 16 | 2.0 | 0.15 | 0.10 | 99.77 | 3.2 | 9.0 |

Examples 17-18 illustrate the surprising ability of the membranes of this invention to remove silica impurities from a feed stock. The results shown in Table 4 illustrate the dissolved silica rejection achieved for the membranes of Examples 1 and 16. Silica rejection is determined by adding 130 ppm of sodium metasilicate nonahydrate to 0.27% NaCl aqueous feed to give 27 ppm dissolved silica as $SiO_2$. Silica rejection is determined at 225 psig as described above for NaCl rejection. Silica concentration in the feed and permeate is determined by Method B of ASTM D 859. The % silica rejection is given below.

TABLE 4

| Example # | Membrane of Example | % Silica Rejection |
|---|---|---|
| 17 | 1 | 99.89 |
| 18 | 16 | 99.53 |

From the foregoing description, one skilled in the art can easily ascertain the essential characteristics of this invention, and without departing from the spirit and scope thereof, can make various changes and modifications of the invention to adapt it to various usages and conditions.

I claim:

1. A method comprising: manufacturing a reverse osmosis membrane that shows improved solute rejection and solvent flux, by,
   casting a polymeric solution into a support to provide a microporous polymeric substrate
   treating said substrate with a polyfunctional amine to provide an impregnated substrate, and
   treating said impregnated substrate with a solution of a haloformyloxy-substituted acyl halide to provide a reverse osmosis membrane with a polyamideurethane separating layer that shows improved solute rejection and solvent flux.

2. The method of claim 1 wherein said support is selected from the group of porous glass, sintered metal, ceramics, and organic polymers.

3. The method of claim 2 wherein said organic polymers are selected from the group of polyolefins, polyesters, and polyamides.

4. The method of claim 1 wherein said polyfunctional amine is selected from the group of m-phenylenediamine, p-phenylenediamine, piperazine, m-xylylenediamine, or mixtures thereof.

5. The method of claim 4 wherein said haloformyloxy-substituted acyl halide is selected from the group of 5-bromoformyloxyisophthaloyl dibromide, 4-chloroformyloxyisophthaloyl chloride, 2-chloroformyloxyisophthaloyl chloride, and 5-chloroformyloxyisophthaloyl chloride.

6. The method of claim 5 wherein said haloformyloxy-substituted acyl halide is employed in combination with isophthaloyl chloride, terephthaloyl chloride or a blend thereof.

7. The method of claim 6 wherein said haloformyloxy-substituted acyl halide is 5-chloroformyloxyisophthaloyl chloride.

8. The method of claim 5 wherein said solution of haloformyloxy-substituted acyl halide includes a solvent selected from the group of 1,1,2-trichlorotrifluoroethane, n-alkanes, and cycloalkanes.

9. The method of claim 8 wherein said solvent is 1,1,2-trichlorotrifluoroethane.

10. The method of claim 4 wherein said polyfunctional amine is m-phenylenediamine.

11. The method of claim 10 wherein said haloformyloxy-substituted acyl halide is 5-chloroformyloxyisophthaloyl chloride.

12. The method of claim 11 wherein said polymeric substrate is polysulfone.

13. The method of claim 1 wherein said polyamideurethane is of the formula:

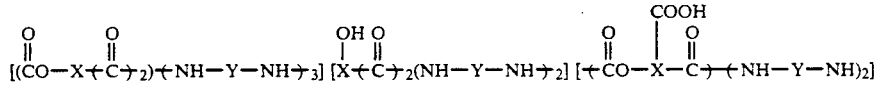

where
X = a trivalent organic group, and
Y = a divalent organic group.

14. The method of claim 13 wherein said X is selected from the group of tri substituted cyclo hexane, tri substituted benzene, tri substituted naphthalene, tri substituted cyclo pentane, tri substituted cyclo heptane.

15. The method of claim 14 wherein said Y is selected from the group of m-phenylene diamine, p-phenylene diamine, piperazine.

16. The method of claim 13 wherein said X is tri substituted benzene and said Y is m-phenylene diamine.

17. A reverse osmosis membrane comprising a polyamideurethane separating layer on a polymeric substrate having properties enabling improved salt rejection, flux and productivity and having properties for enabling improved salt rejection, flux and productivity.

18. The reverse osmosis membrane of claim 17 wherein said polyamideurethane is of the formula:

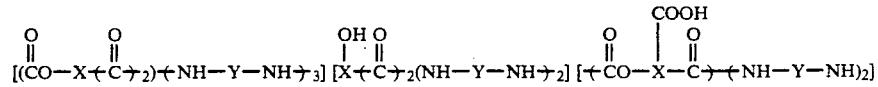

where
X = a trivalent organic group, and
Y = a divalent organic group.

19. The reverse osmosis membrane of claim 18 wherein said substrate is polysulfone.

20. The reverse osmosis membrane of claim 19 wherein said membrane has a percent salt rejection of at least about 90 percent.

21. The reverse osmosis membrane of claim 18 wherein said membrane has a percent salt rejection of at least about 99 percent.

22. The membrane of claim 18 wherein said X is selected from the group of tri substituted cyclo hexane, tri substituted benzene, tri substituted naphthalene, tri substituted cyclo pentane, tri substituted cyclo heptane.

23. The membrane of claim 22 wherein said Y is selected from the group of m-phenylene diamine, p-phenylene diamine, piperazine.

24. The membrane of claim 18 wherein X is tri-substituted benzene and Y is m-phenylene diamine.

25. The reverse osmosis membrane of claim 17 further comprising a polymeric substrate in contact with a support member selected from the group of porous glass, sintered metal, ceramics, and organic polymer.

26. The reverse osmosis membrane of claim 25 wherein said organic polymer is polyester.

27. The reverse osmosis membrane of claim 17 wherein said membrane is in the form of a fiber.

* * * * *

UNITED STATES PATENT AND TRADEMARK OFFICE
CERTIFICATE OF CORRECTION

PATENT NO. : 5,085,777

DATED : Feb. 4, 1992

INVENTOR(S) : Arthur

It is certified that error appears in the above-identified patent and that said Letters Patent is hereby corrected as shown below:

On the title page, change the Appl. No. from "586,038" to
-- 576,038 --.

In column 8, lines 52 and 53, delete "and having properties for enabling improved salt rejection, flux and productivity".

In column 10, add claims 28 and 29 as follows:

-- 28. In a process for desalination of saline water by reverse osmosis comprising contacting the saline water under pressure with a reverse osmosis membrane, the improvement comprising using a reverse osmosis membrane comprising a polyamide urethane separating layer on a polymeric substrate and having properties for enabling improved salt rejection, flux and productivity.

29. In a process for removal of impurities from a liquid selected from the group of milk and fruit juice by reverse osmosis comprising, contacting said liquid under pressure with a reverse osmosis membrane, the improvement comprising using a reverse osmosis membrane comprising a polyamide urethane separating layer on a polymeric substrate and having properties

UNITED STATES PATENT OFFICE
CERTIFICATE OF CORRECTION

PATENT NO. : 5,085,777
DATED : Feb. 4, 1992
INVENTOR(S) : Arthur

It is certified that error appears in the above-identified patent and that said Letters Patent is hereby corrected as shown below:

for enabling improved salt rejection, flux and productivity. --

Signed and Sealed this

Fourth Day of May, 1993

Attest:

MICHAEL K. KIRK

Attesting Officer     Acting Commissioner of Patents and Trademarks